United States Patent
Doi et al.

(10) Patent No.: US 7,875,271 B2
(45) Date of Patent: Jan. 25, 2011

(54) OPHTHALMIC COMPOSITION COMPRISING XANTHAN GUM AND GLUCOSE

(75) Inventors: Koji Doi, Kobe (JP); Hiroshi Aki, Kobe (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 12/225,255

(22) PCT Filed: Mar. 23, 2007

(86) PCT No.: PCT/JP2007/056072
§ 371 (c)(1),
(2), (4) Date: Oct. 21, 2008

(87) PCT Pub. No.: WO2007/108541
PCT Pub. Date: Sep. 27, 2007

(65) Prior Publication Data
US 2009/0269369 A1 Oct. 29, 2009

(30) Foreign Application Priority Data
Mar. 23, 2006 (JP) .............................. 2006-081463

(51) Int. Cl.
*A61K 31/74* (2006.01)
(52) U.S. Cl. ............................................ 424/78.04
(58) Field of Classification Search ............... None
See application file for complete search history.

(56) References Cited

U.S. PATENT DOCUMENTS

| 4,136,177 | A | 1/1979 | Lin et al. | |
|---|---|---|---|---|
| 5,236,951 | A * | 8/1993 | Manara | ................. 514/510 |
| 6,156,785 | A | 12/2000 | Stefansson et al. | |
| 6,174,524 | B1 | 1/2001 | Bawa et al. | |
| 6,264,935 | B1 | 7/2001 | Chastaing et al. | |
| 6,277,365 | B1 | 8/2001 | Ellis et al. | |
| 2002/0094981 | A1 | 7/2002 | Ponticello et al. | |
| 2005/0202983 | A1* | 9/2005 | Xia et al. | ................. 510/119 |
| 2005/0234011 | A1 | 10/2005 | Mazzone et al. | |
| 2005/0234075 | A1 | 10/2005 | Fleenor et al. | |

FOREIGN PATENT DOCUMENTS

| EP | 0 628 314 | | 12/1994 |
|---|---|---|---|
| EP | 1 358 883 | | 11/2003 |
| EP | 1358883 | A1 * | 11/2003 |
| JP | 7-048262 | | 2/1995 |
| WO | 93/21928 | | 11/1993 |
| WO | 99/00133 | | 1/1999 |
| WO | 00/04898 | | 2/2000 |
| WO | 00/04899 | | 2/2000 |
| WO | 03/092584 | | 11/2003 |

* cited by examiner

*Primary Examiner*—Christopher R Tate
*Assistant Examiner*—Deborah A. Davis
(74) *Attorney, Agent, or Firm*—Wenderoth, Lind & Ponack, L.L.P.

(57) ABSTRACT

The present invention provides an ophthalmic composition containing xanthan gum and glucose, which has a superior corneal epithelial disorder-treating effect.

7 Claims, No Drawings

OPHTHALMIC COMPOSITION COMPRISING XANTHAN GUM AND GLUCOSE

This application is a U.S. national stage of International Application No. PCT/JP2007/056072 filed Mar. 23, 2007.

TECHNICAL FIELD

The present invention relates to an ophthalmic composition comprising xanthan gum and glucose, which is used for the treatment of a corneal epithelial disorder.

BACKGROUND ART

Lacrimal fluid covers eye ball surface consisting of cornea and conjunctiva to maintain wettability of the cornea and conjunctiva, and prevents drying. In recent years, however, an increasing number of people report various symptoms including feeling of fatigue and foreign sensation, namely, dry eye syndromes, which are caused by dry surface of cornea and conjunctiva due to decreased lacrimal fluid, dryness of eye during wearing contact lenses, or dryness of eye during operation of OA equipment and the like. Dry eye sometimes accompanies corneal epithelial disorder, corneal epithelial erosion and the like due to disorders of corneal epithelial cells. In a serious case, corneal ulcer and eye infection may be developed. To mitigate such various conditions caused by drying, artificial lacrimal fluids containing salts such as sodium chloride and the like as a main ingredient, eye drops containing hydroxyethylcellulose, chondroitin sulfate or hyaluronic acid and the like have been used. As the situation stands, however, there is no satisfactory agent as yet.

Lacrimal fluid is said to show pseudoplasticity. That is, the viscosity of lacrimal fluid decreases when a force is applied by blinking, and increases when the force is not applied. Therefore, lacrimal fluid has unique property in that it has low viscosity and becomes thin during blinking to facilitate blinking, but it becomes highly viscose before and after blinking to cover the eye surface for protection. As a polymer compound showing such pseudoplasticity, xanthan gum is known.

As an ophthalmic composition comprising xanthan gum, the following have been reported. For example, in patent reference 1, an ophthalmic composition containing echothiopate iodide and xanthan gum is disclosed, and xanthan gum has been reported to enhance the treatment effect of echothiopate iodide. In patent references 2, 3 and 4, an ophthalmic composition comprising xanthan gum and a carbonate dehydratase inhibitor has been disclosed, where xanthan gum is used to improve ophthalmic bioavailability of the carbonate dehydratase inhibitor. In patent references 5, 6 and 7, xanthan gum is used for the purpose of improving ophthalmic bioavailability of a drug, and an ophthalmic composition containing a carbonate dehydratase inhibitor and xanthan gum, or a prostaglandin derivative and xanthan gum, has also been disclosed. In patent reference 8, an ophthalmic composition containing quaternary nitrogen-containing ethoxylated glycoside and xanthan gum has been disclosed for the treatment of dry eye. In patent reference 9, an ophthalmic composition comprising xanthan gum, which is gelated upon contact with the eye, is disclosed. In patent reference 10, a pharmaceutical composition comprising xanthan gum as a re-epithelializing agent is disclosed.

In patent reference 11, an agent for suppressing the development of a corneal epithelial damage, which contains glucose as an active ingredient, is disclosed.

However, no report is found on an ophthalmic composition comprising xanthan gum and glucose. Moreover, it is not known that a corneal epithelial cell-protecting action can be improved by combining xanthan gum and glucose.

patent reference 1: U.S. Pat. No. 4,136,177
patent reference 2: JP-2001-508035
patent reference 3: JP-2002-501017
patent reference 4: JP-2002-506461
patent reference 5: JP-2002-501533
patent reference 6: JP-2002-521332
patent reference 7: JP-2002-521333
patent reference 8: JP-2001-516713
patent reference 9: JP-2002-510654
patent reference 10: JP-2005-529906
patent reference 11: JP-A-7-048262

DISCLOSURE OF THE INVENTION

Problems to be Solved by the Invention

An object of the present invention is to provide an ophthalmic composition having good usability and a superior treatment effect for corneal epithelial disorders. Specifically, the object is to provide an ophthalmic composition having a superior corneal epithelial cell-protecting effect.

Means of Solving the Problems

The present inventors have conducted intensive studies in an attempt to achieve the above-mentioned object and found that, in a culture test system of corneal epithelial cells, a cell protecting action can be improved by combining xanthan gum and glucose, based on which finding they have proceeded further with the studies and completed the present invention.

Accordingly, the present invention relates to:

(1) an ophthalmic composition comprising xanthan gum and glucose,
(2) the ophthalmic composition of the aforementioned (1), wherein the concentration of the xanthan gum therein is 0.05-0.5 w/v %,
(3) the ophthalmic composition of the aforementioned (1) or (2), wherein the concentration of the glucose therein is 0.001-0.1 W/V %,
(4) the ophthalmic composition of any one of the aforementioned (1) to (3), which is used for the treatment of a corneal epithelial disorder,
(5) the ophthalmic composition of the aforementioned (4), wherein the corneal epithelial disorder is a disorder in a corneal epithelial cell,
(6) the ophthalmic composition of any one of the aforementioned (1) to (3), which is used for protecting a corneal epithelial cell,
(7) the ophthalmic composition of any one of the aforementioned (1) to (6), which is an eye drop,
(8) use of xanthan gum and glucose for the production of the composition of any one of the aforementioned (4) to (6) or the eye drop of the aforementioned (7),
(9) the use of the aforementioned (8), wherein the concentration of the xanthan gum is 0.05-0.5 w/v %,
(10) the use of the aforementioned (8) or (9), wherein the concentration of the glucose is 0.001-0.1 w/v %,
(11) a method of treating a corneal epithelial disorder, which comprises a step of administering effective amounts of xanthan gum and glucose to an administration subject in need of the treatment,

(12) a method of protecting a corneal epithelial cell, which comprises a step of administering effective amounts of xanthan gum and glucose to an administration subject in need of the protection,
(13) the method of the aforementioned (11) or (12), wherein the concentration of the xanthan gum is 0.05-0.5 w/v %, and
(14) the method of any one of the aforementioned (11) to (13), wherein the concentration of the glucose is 0.001-0.1 w/v %.

EFFECT OF THE INVENTION

According to the present invention, an ophthalmic composition comprising xanthan gum and glucose, having a superior effect of treating a corneal epithelial disorder, can be provided. Moreover, the ophthalmic composition of the present invention in the form of an eye drop has superior usability since it contains xanthan gum showing pseudoplasticity.

BEST MODE FOR CARRYING OUT THE INVENTION

The present invention is explained in more detail in the following.

The present invention can provide an ophthalmic composition comprising xanthan gum and glucose. In the following, such ophthalmic compositions are also collectively referred to as the ophthalmic composition of the present invention.

The ophthalmic composition of the present invention only needs to be a preparation that can be administered to a topical tissue of the eye, and examples thereof include eye drop, plaster and pressure sensitive adhesive, ointment, lotion, cream and the like, with preference given to an eye drop. Moreover, the ophthalmic composition of the present invention can also be used as a contact lens solution, an artificial lacrimal fluid, an eye lotion and the like.

The xanthan gum to be used for the ophthalmic composition of the present invention has an average molecular weight of generally 100000-50000000, preferably 200000-20000000, particularly preferably 1000000-10000000. As the xanthan gum, ECHO GUM series such as ECHO GUM T, ECHO GUM F and the like commercially available from Dainippom Sumitomo Pharma Co., Ltd., SAN-ACE series such as SAN-ACE NXG-S and the like commercially available from San-Ei Gen F.F.I. Inc., KELTROL series such as KELTROL CG, KELTROL CG-T and the like commercially available from Sansho Co., Ltd., and the like are used, with preference given to ECHO GUM T and KELTROL CG-T.

The content of xanthan gum in the ophthalmic composition of the present invention is generally 0.005-1 w/v %, preferably 0.01-0.6 w/v %, more preferably 0.05-0.5 w/v %, particularly preferably 0.05-0.2 w/v %.

The content of glucose in the ophthalmic composition of the present invention is generally 0.0005-5 w/v %, preferably 0.001-2 w/v %, more preferably 0.001-0.1 w/v %, particularly preferably 0.005-0.1 w/v %.

The dose of xanthan gum may vary depending on the dosage form, target disease, age, sex, body weight of the test subject, symptom and the like. For an adult (e.g., body weight 60 kg), for example, the dose is generally within the range of 0.25 mg-5 mg, preferably 0.25 mg-2 mg, per day.

In addition, the does of glucose may vary depending on the dosage form, target disease, age, sex, body weight of the test subject, symptom and the like. For an adult (e.g., body weight 60 kg), for example, the dose is generally within the range of 0.001 mg-0.1 mg, preferably 0.002 mg-0.02 mg, per day.

When xanthan gum and glucose are to be administered and they can be combined on administration, they may be administered as a single preparation obtained by simultaneously formulating xanthan gum and glucose into a preparation, or may be simultaneously administered as a combination of two kinds of preparations obtained by separately formulating xanthan gum and glucose into preparations.

The proportion of the combination of xanthan gum and glucose is generally within the range of 500:1-1:1, preferably 100:1-10:1, in weight ratio, for both the administration of a single preparation and the administration of separate preparations.

The daily dose of each component can be administered at once or in several portions. For use as an eye drop, for example, the ophthalmic composition of the present invention can be administered in several portions, preferably 1-6 portions, a day, by several drops, preferably 1-3 drops, one time. In addition, duration of the administration is not particularly limited.

The ophthalmic composition of the present invention can contain various additives as appropriate, such as buffer, isotonicity agent, preservative, solubilizing agents, stabilizer, chelating agent, thickener, pH adjuster, algefacient and the like.

The ophthalmic composition of the present invention may contain, as long as not opposing the object, one or more kinds of efficacious components selected from anti-inflammatory agents (allantoin, pranoprofen etc.), decongestants (naphazoline hydrochloride etc.), ocular regulators (neostigmine methylsulfate etc.), astringent agents (zinc sulfate etc.), antihistamine agents (chlorpheniramine maleate, diphenhydramine hydrochloride etc.), antiallergic agents (sodium cromoglycate etc.), vitamins (tocopherol acetate, flavin adenine dinucleotide sodium, pyridoxine hydrochloride, cyanocobalamin, panthenol etc.), sulfa drugs (sulfamethoxazole etc.), sodium chondroitin sulfate, amino acid and the like.

As the buffer, for example, boric acid or a salt thereof (sodium borate etc.), citric acid or a salt thereof (sodium citrate etc.), tartaric acid or a salt thereof (sodium tartrate etc.), gluconic acid or a salt thereof (sodium gluconate etc.), acetic acid or a salt thereof (sodium acetate etc.), phosphoric acid or a salt thereof (sodium hydrogenphosphate, sodium dihydrogenphosphate etc.), various amino acids such as glutamic acid, $\epsilon$-aminocaproic acid and the like and tris buffer etc., and a combination thereof can be mentioned.

As the isotonicity agent, for example, sorbitol, mannitol, glycerol, propylene glycol, sodium chloride, potassium chloride and the like can be mentioned.

As the preservative, for example, paraoxybenzoates, benzalkonium chloride, benzethonium chloride, benzyl alcohol, sorbic acid or a salt thereof, chlorhexidine gluconate, sodium dehydroacetate, cetylpyridinium chloride, alkyldiaminoethylglycine hydrochloride, chlorobutanol, polyhexamide hydrochloride and the like can be mentioned.

As the solubilizing agent, for example, polyvinylpyrrolidone, polyethylene glycol, propylene glycol, polyoxyethylene hydrogenated castor oil 60, polyoxy 40 stearate, polysorbate 80 (trade name: Tween 80) and the like can be mentioned.

As the stabilizer, for example, disodium edetate, thiosodium sulfate, ascorbic acid, cyclodextrin, condensed phosphoric acid or a salt thereof, sulfite, citric acid or a salt thereof, dibutylhydroxytoluene and the like can be mentioned.

As the chelating agent, for example, disodium edetate, sodium citrate, condensed phosphoric acid or a salt thereof (sodium condensed phosphate etc.) and the like can be mentioned.

As the thickener, for example, methylcellulose, hydroxyethylcellulose, hydroxypropylcellulose, hydroxypropylmethylcellulose, sodium carboxymethylcellulose, polyvinylpyrrolidone, polyvinyl alcohol, polyethylene glycol, hyaluronic acid and the like can be mentioned.

As the pH adjuster, for example, sodium hydroxide, potassium hydroxide, sodium carbonate, sodium hydrogen carbonate, boric acid or a salt thereof (sodium borate), hydrogen chloride, citric acid or a salt thereof (sodium citrate, sodium dihydrogen citrate etc.), phosphoric acid or a salt thereof (disodium hydrogen phosphate, potassium dihydrogen phosphate etc.), acetic acid or a salt thereof (sodium acetate, ammonium acetate etc.), tartaric acid or a salt thereof (sodium tartrate etc.) and the like can be mentioned.

As the algefacient, for example, l-menthol, dl-camphor, borneol, geraniol, eucalyptus oil and the like can be mentioned.

As the amino acid, for example, glycine, alanine, valine, leucine, isoleucine, phenylalanine, proline, serine, threonine, tyrosine, asparagine, glutamine, lysin, arginine, tryptophan, histidine, cysteine, methionine, aspartic acid, glutamic acid, aminoethylsulfonic acid, and a pharmacologically acceptable salt thereof can be mentioned. As the salt, for example, sodium salt, potassium salt, calcium salt and magnesium salt can be mentioned.

The ophthalmic composition of the present invention is adjusted to have pH 3-10, preferably pH 5-9.

The ophthalmic composition of the present invention has a corneal epithelial cell protecting action. Accordingly, the ophthalmic composition of the present invention is useful as an agent for the prophylaxis or treatment of a corneal epithelial disorder, particularly a corneal epithelial cell disorder associated with a corneal epithelial disorder. In particular, the ophthalmic composition of the present invention is useful as an agent for the prophylaxis or treatment of corneal epithelial disorders caused by drying (e.g., lacrimal fluid decrease symptom, xerophthalmia, meibomian gland dysfunction, Sjogren's syndrome, keratoconjunctivitis sicca, blepharitis, Stevens-Johnson syndrome, dry eye syndrome such as dry eye and the like related to VDT (Visual Display Terminal) operations, corneal and conjunctival epithelial disorder caused by dry eye, corneal epithelial erosion, corneal ulcer, blepharitis, ocular pemphigus, vernal kerato-conjunctivitis, allergic conjunctivitis etc.), particularly as an agent for the prophylaxis or treatment of a corneal epithelial cell disorder associated with a corneal epithelial disorder caused by drying.

The ophthalmic composition of the present invention can also be used as an instillation composition for the prophylaxis or improvement of eye fatigue, dryness of eye, blurred vision, eye irritation, conjunctival injection, uncomfortableness by wearing contact lenses and the like.

The ophthalmic composition of the present invention can be used for the prophylaxis or treatment of the above-mentioned diseases or conditions in human and animals other than human [e.g., mammals other than human (domestic animals and pets such as swine, bovine, horse, dog etc.) and the like].

The present invention provides a method of preventing or treating the above-mentioned diseases or conditions, particularly, a method of treating corneal epithelial disorder and a method of protecting corneal epithelial cells, wherein the methods include a step of administering effective amounts of xanthan gum and glucose to an administration subject (e.g., human or animal other than human) in need of the treatment or protection.

The present invention further provides a kit (commercial package) to be used for practicing the above-mentioned method. The kit contains the ophthalmic composition of the present invention, and further, a written matter stating that the composition can be used (or should be used) for the prophylaxis or treatment of the above-mentioned diseases or conditions, or that the composition can be used (or should be used) for the treatment of a corneal epithelial disorder and the like (e.g., instruction sheet for practicing the above-mentioned method using the kit).

The present invention is explained in detail in the following by referring to Examples and Experimental Examples, which are not to be construed as limitative.

EXAMPLES

Experimental Example 1

Corneal Epithelial Cell Protecting Action by a Combination of Xanthan Gum and Glucose 1. Experimental Method This experiment was performed as described (Br. J. Opthalmol. 2001, 85, 610). A frozen normal rabbit corneal epithelial cell suspension (NRCE2, manufactured by Kurabo Industries Ltd.) was suspended in a culture medium (RCGM2, manufactured by Kurabo Industries Ltd.). This suspension was centrifuged (5 min, 400×g), and the supernatant was removed. The cells were suspended in 2 mL of a culture medium, 20 µL thereof was diluted with 20 µL of trypan blue, and viable cells were counted on a blood cell counting chamber. Then, the cells were inoculated to each well of a 96-well plate to $4 \times 10^3$ cells/well/µL, and cultured to confluence at 37° C., 5% $CO_2$ under moisturization (n=5). The culture supernatant was removed from the 96-well plate, 100 µL of phosphate buffer (pH 7, test solution) containing various concentrations (w/v %) of glucose and/or xanthan gum (ECHO GUM T: trademark) or phosphate buffer (pH 7, control solution) was added, and the mixture was cultured at 37° C., 5% $CO_2$ under moisturization for 15 min. After culture, the added test solution or control solution was removed, and the cells were dried at room temperature for 30 min. A Cell Counting Kit-8 solution (100 µL, manufactured by DOJINDO LABORATORIES) was added to each well, and absorbance (wavelength 450 nm) was measured 2 hr later using a 96-well Microplate Reader (Labsystems Multiskan, trademark). The survival rate (%) of the corneal epithelial cell was determined using the following formula from the average value of absorbance of the test solution or control solution and the average value of absorbance of the non-treatment group.

$$\text{Survival rate (\%)} = \frac{\text{average value of absorbance of test solution or control solution addition group}}{\text{average value of absorbance of non-treatment group}} \times 100$$

The drying condition after culture needs to be set to an appropriate temperature and time according to the concentrations of xanthan gum and glucose. Preferable drying conditions include a temperature of 15° C.-50° C. and a time period of 10 min-180 min.

2. Experimental Results

As shown in Table 1, the survival rate of the corneal epithelial cell treated with a 0.005% or 0.1% glucose solution containing 0.1% xanthan gum showed a higher value as compared to that of the cell treated with a glucose solution without xanthan gum. In addition, the survival rate when treated with a phosphate buffer containing 0.1% xanthan gum (xanthan gum alone solution) stayed about the same as that of the cell treated with a mere phosphate buffer without xanthan gum. The survival rate-improving effect by the addition of xanthan gum (difference in the survival rate between addition and non-addition of xanthan gum) was higher with the glucose solution than with the phosphate buffer.

The results indicate that a combination of xanthan gum and glucose improves a corneal epithelial cell protecting action.

TABLE 1

| | survival rate | | survival rate- |
| --- | --- | --- | --- |
| | xanthan gum non-addition (A) | xanthan gum addition (B) | improving effect (B − A, %) |
| 0.1% glucose | 17.2 | 94.6 | 77.4 |
| 0.005% glucose | 17.2 | 115.9 | 98.7 |
| phosphate buffer | 32.1 | 32.6 | 0.5 |

Preparation Examples of the eye drops containing xanthan gum and glucose according to the present invention are shown in below.

Example 1

Artificial Lacrimal Fluid

An artificial lacrimal fluid having the following formulation was prepared by a conventional method.

| | |
| --- | --- |
| sodium chondroitin sulfate | 0.5 g |
| sodium chloride | 0.5 g |
| glucose | 0.005 g |
| boric acid | 0.3 g |
| sodium borate | e.q. |
| sodium citrate | 0.2 g |
| xanthan gum | 0.5 g |
| sorbic acid | 0.2 g |
| purified water | e.q. |
| total amount | 100 ml (pH 7.0) |

Example 2

Artificial Lacrimal Fluid

An artificial lacrimal fluid having the following formulation was prepared by a conventional method.

| | |
| --- | --- |
| potassium L-aspartate | 1 g |
| sodium chloride | 0.5 g |
| glucose | 0.001 g |
| boric acid | 0.2 g |
| sodium borate | e.q. |
| xanthan gum | 0.2 g |
| benzalkonium chloride solution (10 w/v %) (as benzalkonium chloride 0.005 g) | 0.05 ml |
| purified water | e.q. |
| total amount | 100 ml (pH 7.2) |

Example 3

Artificial Lacrimal Fluid

An artificial lacrimal fluid having the following formulation was prepared by a conventional method.

| | |
| --- | --- |
| sodium chloride | 0.5 g |
| glucose | 0.1 g |
| boric acid | 0.4 g |
| sodium borate | e.q. |
| disodium edetate | 0.01 g |
| xanthan gum | 0.1 g |
| hydroxypropylmethylcellulose 2910 | 0.2 g |
| benzalkonium chloride solution (10 w/v %) (as benzalkonium chloride 0.005 g) | 0.05 ml |
| purified water | e.q. |
| total amount | 100 ml (pH 7.2) |

Example 4

Eye Drops for Contact Lenses

Eye drops for contact lenses having the following formulation were prepared by a conventional method.

| | |
| --- | --- |
| sodium chondroitin sulfate | 0.5 g |
| sodium chloride | 0.55 g |
| potassium chloride | 0.15 g |
| glucose | 0.005 g |
| boric acid | 0.5 g |
| sodium borate | e.q. |
| disodium edetate | 0.01 g |
| xanthan gum | 0.1 g |
| polysorbate 80 | 0.15 mL |
| hydroxyethylcellulose | 0.5 g |
| chlorhexidine gluconate solution (20 w/v %) (as chlorhexidine gluconate 0.005 g) | 0.025 mL |
| purified water | e.q. |
| total amount | 100 ml (pH 7.2) |

Example 5

Contact Lens Solution

A contact lens solution having the following formulation was prepared by a conventional method.

| | |
| --- | --- |
| aminoethyl sulfonic acid | 1 g |
| partially hydrolyzed polyvinyl alcohol | 2 g |
| sodium chloride | 0.6 g |
| hydroxypropylmethylcellulose 2906 | 0.5 g |
| glucose | 0.005 g |

-continued

| | |
|---|---|
| disodium edetate | 0.02 g |
| sodium acetate | 0.1 g |
| sodium hydroxide | e.q. |
| xanthan gum | 0.1 g |
| benzalkonium chloride solution (10 w/v %) (as benzalkonium chloride 0.005 g) | 0.05 mL |
| purified water | e.q. |
| total amount | 100 ml (pH 7.2) |

Example 6

Artificial Lacrimal Fluid

An artificial lacrimal fluid having the following formulation was prepared by a conventional method.

| | |
|---|---|
| sodium chondroitin sulfate | 0.5 g |
| sodium chloride | 0.5 g |
| glucose | 0.05 g |
| boric acid | 0.3 g |
| sodium borate | e.q. |
| sodium citrate | 0.2 g |
| xanthan gum | 0.3 g |
| sorbic acid | 0.2 g |
| purified water | e.q. |
| total amount | 100 ml (pH 7.0) |

Example 7

Artificial Lacrimal Fluid

An artificial lacrimal fluid having the following formulation was prepared by a conventional method.

| | |
|---|---|
| potassium L-aspartate | 1 g |
| sodium chloride | 0.5 g |
| glucose | 0.005 g |
| boric acid | 0.2 g |
| sodium borate | e.q. |
| xanthan gum | 0.2 g |
| benzalkonium chloride solution (10 w/v %) (as benzalkonium chloride 0.005 g) | 0.05 ml |
| purified water | e.q. |
| total amount | 100 ml (pH 7.2) |

Example 8

Artificial Lacrimal Fluid

An artificial lacrimal fluid having the following formulation was prepared by a conventional method.

| | |
|---|---|
| aminoethyl sulfonic acid | 1 g |
| sodium chloride | 0.5 g |
| glucose | 0.025 g |
| boric acid | 0.4 g |
| sodium borate | e.q. |
| xanthan gum | 0.5 g |

-continued

| | |
|---|---|
| benzalkonium chloride solution (10 w/v %) (as benzalkonium chloride 0.005 g) | 0.05 ml |
| purified water | e.q. |
| total amount | 100 ml (pH 7.2) |

Example 9

Eye Drops for Contact Lenses

Eye drops for contact lens having the following formulation was prepared by a conventional method.

| | |
|---|---|
| sodium chondroitin sulfate | 0.5 g |
| sodium chloride | 0.55 g |
| potassium chloride | 0.15 g |
| glucose | 0.1 g |
| boric acid | 0.5 g |
| sodium borate | e.q. |
| disodium edetate | 0.01 g |
| xanthan gum | 0.5 g |
| polysorbate 80 | 0.15 mL |
| chlorhexidine gluconate solution (20 w/v %) (as chlorhexidine gluconate 0.005 g) | 0.025 mL |
| purified water | e.q. |
| total amount | 100 ml (pH 7.2) |

Example 10

Contact Lens Solution

A contact lens solution having the following formulation was prepared by a conventional method.

| | |
|---|---|
| potassium L-aspartate | 1 g |
| partially hydrolyzed polyvinyl alcohol | 2 g |
| sodium chloride | 0.4 g |
| hydroxypropylmethylcellulose 2906 | 0.5 g |
| glucose | 0.01 g |
| disodium edetate | 0.02 g |
| sodium acetate | 0.1 g |
| sodium hydroxide | e.q. |
| xanthan gum | 0.4 g |
| benzalkonium chloride solution (10 w/v %) (as benzalkonium chloride 0.005 g) | 0.05 mL |
| purified water | e.q. |
| total amount | 100 ml (pH 7.2) |

Example 11

Contact Lens Solution

A contact lens solution having the following formulation was prepared by a conventional method.

| | |
|---|---|
| aminoethyl sulfonic acid | 1 g |
| partially hydrolyzed polyvinyl alcohol | 2 g |
| povidone | 2.5 g |
| sodium chloride | 0.6 g |

-continued

| | |
|---|---|
| hydroxypropylmethylcellulose 2906 | 0.5 g |
| glucose | 0.005 g |
| disodium edetate | 0.02 g |
| sodium acetate | 0.1 g |
| sodium hydroxide | e.q. |
| xanthan gum | 0.5 g |
| benzalkonium chloride solution (10 w/v %) (as benzalkonium chloride 0.005 g) | 0.05 mL |
| purified water | e.q. |
| total amount | 100 ml (pH 7.2) |

Example 12

Non-prescription Ophthalmic Solution

A non-prescription ophthalmic solution of the following formulation was prepared according to a conventional method.

| | |
|---|---|
| neostigmine methylsulfate | 0.005 g |
| panthenol | 0.1 g |
| potassium l-aspartate | 1 g |
| allantoin | 0.1 g |
| chlorpheniramine maleate | 0.03 g |
| sodium chloride | 0.45 g |
| sodium l-glutamate | 0.2 g |
| glucose | 0.1 g |
| polyoxyethylene hydrogenated castor oil 60 | 0.3 g |
| l-menthol | 0.008 g |
| borneol | 0.002 g |
| hydrogen chloride | e.q. |
| benzalkonium chloride | 0.005 g |
| chlorobutanol | 0.2 g |
| xanthan gum | 0.5 g |
| purified water | e.q. |
| total amount | 100 ml (pH 5.5) |

Example 13

Non-prescription Ophthalmic Solution

A non-prescription ophthalmic solution of the following formulation was prepared according to a conventional method.

| | |
|---|---|
| naphazoline hydrochloride | 0.002 g |
| allantoin | 0.1 g |
| zinc sulfate | 0.1 g |
| chlorpheniramine maleate | 0.03 g |
| aminoethyl sulfonic acid | 0.1 g |
| boric acid | 0.7 g |
| ε-aminocaproic acid | 0.2 g |
| sodium chloride | 0.45 g |
| chlorobutanol | 0.15 g |
| methyl paraoxybenzoate | 0.02 g |
| glucose | 0.1 g |
| l-menthol | 0.03 g |
| dl-camphor | 0.003 g |
| *eucalyptus* oil | 0.0009 g |
| geraniol | 0.0009 g |
| macrogol 4000 | 0.3 g |
| xanthan gum | 0.2 g |
| purified water | e.q. |
| total amount | 100 ml (pH 5.8) |

Example 14

Non-prescription Ophthalmic Solution

A non-prescription ophthalmic solution of the following formulation was prepared according to a conventional method.

| | |
|---|---|
| sodium cromoglycate | 1 g |
| chlorpheniramine maleate | 0.015 g |
| pranoprofen | 0.05 g |
| boric acid | 1.8 g |
| sodium borate | 0.35 g |
| dibutylhydroxytoluene | 0.005 g |
| disodium edetate | 0.01 g |
| glucose | 0.1 g |
| benzalkonium chloride | 0.005 g |
| l-menthol | 0.005 g |
| polysorbate 80 | 0.2 g |
| xanthan gum | 0.3 g |
| purified water | e.q. |
| total amount | 100 ml (pH 7.0) |

Example 15

Eye Drop for Contact Lenses

An eye drop for contact lenses of the following formulation was prepared according to a conventional method.

| | |
|---|---|
| sodium chondroitin sulfate | 0.5 g |
| sodium chloride | 0.55 g |
| potassium chloride | 0.15 g |
| glucose | 0.01 g |
| boric acid | 0.5 g |
| sodium borate | e.q. |
| disodium edetate | 0.01 g |
| xanthan gum | 0.3 g |
| sodium hyaluronate | 0.01 g |
| hydroxyethylcellulose | 0.1 g |
| polyhexanide hydrochloride | 0.1 mg |
| purified water | e.q. |
| total amount | 100 mL (pH 7.2) |

Example 16

Sulfa Drug Eye Drop

A sulfa eye drop of the following formulation was prepared according to a conventional method.

| | |
|---|---|
| sulfamethoxazole | 4 g |
| diphenhydramine hydrochloride | 0.05 g |
| disodium edetate | 0.01 g |
| glucose | 0.005 g |
| xanthan gum | 0.2 g |
| sodium hydroxide | e.q. |
| purified water | e.q. |
| total amount | 100 mL (pH 8.5) |

Example 17

Non-prescription Eye Drop

A non-prescription eye drop of the following formulation was prepared according to a conventional method.

| | |
|---|---|
| flavin adenine dinucleotide sodium | 0.05 g |
| pyridoxine hydrochloride | 0.05 g |
| tocopherol acetate | 0.025 g |
| boric acid | 1.8 g |
| sodium borate | e.q. |
| dibutylhydroxytoluene | 0.005 g |
| disodium edetate | 0.01 g |
| glucose | 0.1 g |
| chlorobutanol | 0.15 g |
| benzalkonium chloride | 0.005 g |
| l-menthol | 0.005 g |
| polysorbate 80 | 0.2 g |
| macrogol 4000 | 0.3 g |
| xanthan gum | 0.3 g |
| purified water | e.q. |
| total amount | 100 mL (pH 6.0) |

Example 18

Non-prescription Eye Drop

A non-prescription eye drop of the following formulation was prepared according to a conventional method.

| | |
|---|---|
| ε-aminocaproic acid | 1 g |
| cyanocobalamin | 0.02 g |
| panthenol | 0.1 g |
| tocopherol acetate | 0.025 g |
| boric acid | 1.5 g |
| disodium edetate | 0.01 g |
| glucose | 0.01 g |
| chlorobutanol | 0.15 g |
| benzethonium chloride | 0.005 g |
| l-menthol | 0.005 g |
| hydrogenated polyoxyethylene castor oil 60 | 0.2 g |
| xanthan gum | 0.1 g |
| sodium hydroxide | e.q. |
| purified water | e.q. |
| total amount | 100 mL (pH 6.0) |

Example 19

Eye Lotion

An eye lotion of the following formulation was prepared according to a conventional method.

| | |
|---|---|
| allantoin | 0.03 g |
| chlorpheniramine maleate | 0.003 g |
| pyridoxine hydrochloride | 0.01 g |
| aminoethyl sulfonic acid | 0.1 g |
| boric acid | 1.8 g |
| sodium borate | e.q. |
| disodium edetate | 0.005 g |
| glucose | 0.005 g |
| benzethonium chloride | 0.0025 g |
| l-menthol | 0.005 g |
| xanthan gum | 0.1 g |
| purified water | e.q. |
| total amount | 100 mL (pH 6.0) |

Example 20

Artificial Lacrimal Fluid

An artificial lacrimal fluid of the following formulation was prepared according to a conventional method.

| | |
|---|---|
| potassium l-aspartate | 1 g |
| sodium chloride | 0.5 g |
| glucose | 0.001 g |
| boric acid | 0.2 g |
| sodium borate | e.q. |
| xanthan gum | 0.05 g |
| benzalkonium chloride solution (10 w/v %) | 0.05 mL |
| (0.005 g as benzalkonium chloride) | |
| purified water | e.q. |
| total amount | 100 mL (pH 7.0) |

Example 21

Eye Drop for Contact Lenses

An eye drop for contact lenses of the following formulation was prepared according to a conventional method.

| | |
|---|---|
| sodium chondroitin sulfate | 0.5 g |
| sodium chloride | 0.55 g |
| potassium chloride | 0.15 g |
| glucose | 0.0025 g |
| boric acid | 0.5 g |
| sodium borate | e.q. |
| disodium edetate | 0.01 g |
| xanthan gum | 0.05 g |
| sodium hyaluronate | 0.01 g |
| hydroxyethylcellulose | 0.1 g |
| polyhexanide hydrochloride | 0.1 mg |
| purified water | e.q. |
| total amount | 100 mL (pH 7.0) |

INDUSTRIAL APPLICABILITY

According to the present invention, an ophthalmic composition comprising xanthan gum and glucose, which has a superior corneal epithelial disorder-treating effect and a superior corneal epithelial cell-protecting effect, can be provided. The ophthalmic composition of the present invention is useful as an agent for the prophylaxis or treatment of lacrimal fluid decrease symptom, xerophthalmia, meibomian gland dysfunction, Sjogren's syndrome, keratoconjunctivitis sicca, blepharitis, Stevens-Johnson syndrome, dry eye syndrome such as dry eye and the like related to VDT operations, corneal and conjunctival epithelial disorder caused by dry eye and the like. Moreover, the ophthalmic composition of the present invention in the form of an eye drop has superior usability since it contains xanthan gum showing pseudoplasticity.

While some of the embodiments of the present invention have been described in detail in the above, those of ordinary skill in the art can enter various modifications and changes to the particular embodiments shown without substantially departing from the novel teaching and advantages of the present invention. Such modifications and changes are encompassed in the spirit and scope of the present invention as set forth in the appended claims.

This application is based on application No. 2006-081463 filed in Japan, the contents of which are incorporated hereinto by reference.

The invention claimed is:

1. An ophthalmic composition comprising xanthan gum and glucose, wherein the concentration of the xanthan gum therein is 0.05-0.5 w/v % and the concentration of the glucose therein is 0.001-0.1 w/v %.

2. The ophthalmic composition of claim 1, which is used for the treatment of a corneal epithelial disorder.

3. The ophthalmic composition of claim 2, wherein the corneal epithelial disorder is a disorder in a corneal epithelial cell.

4. The ophthalmic composition of claim 1, which is used for protecting a corneal epithelial cell.

5. The ophthalmic composition of claim 1, which is an eye drop.

6. A method of treating a corneal epithelial disorder, which comprises a step of administering effective amounts of xanthan gum and glucose to a human or an animal other than a human in need of the treatment, wherein the concentration of the xanthan gum is 0.05-0.5 w/v %, and the concentration of the glucose is 0.001-0.1 w/v %.

7. A method of protecting a corneal epithelial cell, which comprises a step of administering effective amounts of xanthan gum and glucose to a human or an animal other than a human in need of the protection, wherein the concentration of the xanthan gum is 0.05-0.5 w/v %, and the concentration of the glucose is 0.001-0.1 w/v %.

* * * * *